United States Patent
Durazo et al.

[19]

[11] Patent Number: 6,122,999
[45] Date of Patent: Sep. 26, 2000

[54] LATHE APPARATUS AND METHOD

[75] Inventors: Armando Durazo, Acworth; Drew Morgan, Woodstock; Charles Mannor, Sugar Hill, all of Ga.

[73] Assignee: Novartis AG, Basel, Switzerland

[21] Appl. No.: 09/060,431

[22] Filed: Apr. 14, 1998

Related U.S. Application Data

[60] Provisional application No. 60/104,590, Apr. 17, 1997.

[51] Int. Cl.$^7$ ...................................................... B23B 1/00
[52] U.S. Cl. .............................. 82/1.11; 82/118; 82/128; 82/134; 82/1.3
[58] Field of Search ................................ 82/1.11, 47, 59, 82/118, 128, 133, 134, 1.3, 1.4; 408/17, 129, 130

[56] References Cited

U.S. PATENT DOCUMENTS

| | | | |
|---|---|---|---|
| 3,754,487 | 8/1973 | Nachtigal | 82/118 X |
| 3,996,823 | 12/1976 | Guillermier | 408/17 X |
| 4,095,878 | 6/1978 | Fanti | 351/161 |
| 4,680,998 | 7/1987 | Council | 82/1 |
| 4,884,482 | 12/1989 | Council | 82/1.11 |
| 4,947,715 | 8/1990 | Council | 82/1.11 |
| 5,181,442 | 1/1993 | Nezu | 82/118 X |
| 5,195,407 | 3/1993 | Takeno et al. | 82/118 X |
| 5,396,821 | 3/1995 | Okumura et al. | 82/134 X |
| 5,417,130 | 5/1995 | Dorsch | 82/118 X |

FOREIGN PATENT DOCUMENTS 0 439 425 A1  1/1995  European Pat. Off. .

OTHER PUBLICATIONS

Variform Toric Generator, Rank Pneumo, Keene, NH 03430 publication.

*Primary Examiner*—Henry W. H. Tsai
*Attorney, Agent, or Firm*—R. Scott Meece; Richard I. Gearhart

[57] ABSTRACT

In one form, the disclosure describes a lathe apparatus and method for manufacturing a product with a non-axisymmetric shape from a workpiece, such as a toric contact lens, comprises a spindle for rotating the workpiece about an axis of rotation, a cutting tool, a two-axis bed for supporting the cutting tool and for moving the cutting tool along a predetermined path adjacent the workpiece as the spindle rotates the workpiece, and a mechanism for oscillating the cutting tool along an oscillation axis as the two-axis bed moves the cutting tool along the predetermined path, wherein the oscillation axis is oriented at a non-zero angle with respect to the axis of rotation. Preferably, the non-zero angle is about 45°. In a second form, a lathe apparatus comprises a rotary bed for arcuately moving a cutting tool adjacent a workpiece and a mechanism for translationally reciprocating the cutting tool as the cutting tool is arcuately moved adjacent the workpiece.

9 Claims, 5 Drawing Sheets

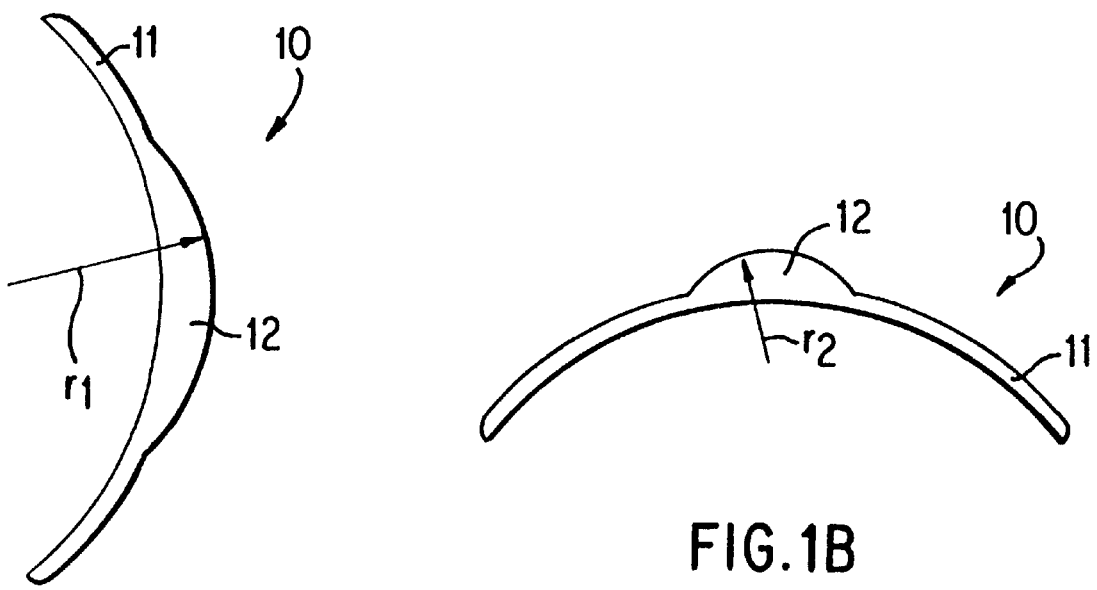
FIG.1A
FIG.1B
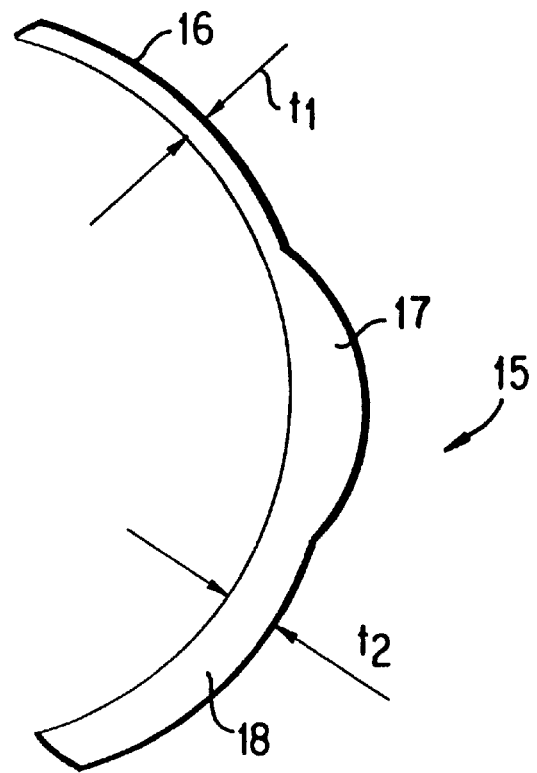
FIG.1C

LATHE APPARATUS AND METHOD

This Appln claims the benefit of U.S. Provisional No. 60/104,590 filed Apr. 17, 1997.

TECHNICAL FIELD

The present invention relates generally to the field of machining three-dimensional surfaces on workpieces and in particular relates to a lathe apparatus and method for machining non-axisymmetric surfaces on workpieces, such as contact lenses.

BACKGROUND OF THE INVENTION

Some people are lucky enough to have near-perfect vision which requires no optical correction. However, a great many people suffer from one or more visual impairments. For example, some people suffer from hypermetropia (farsightedness) in which light images nearer than a certain distance cannot be focused properly on the retina, but instead are focused behind it. Other people suffer from myopia or nearsightedness. The visual impairments just described typically can be corrected using contact lenses having spherical surfaces. However, a good many other visual impairments require contact lenses which have aspherical surfaces. For example, astigmatism, a common malady, requires the use of non-axisymmetric lens surfaces. Astigmatism is a refractive defect in which the curvature of the eye is different in one direction than it is in another direction. To correct this then, a contact lens is required having surfaces with differing curvature radii in order to compensate for the astigmatism. Oftentimes, the astigmatism is coupled with nearsightedness or farsightedness so that the contact lenses required need to correct both conditions.

In the past, one way of providing contact lenses with both spherical surfaces and aspherical surfaces has been to machine and polish a spherical correction onto a concave inner surface of a lens and thereafter to crimp the lens in a holding device to oblate the lens. The thus-oblated lens is then machined and polished on the convex outer surface. After the lens is released from the crimping device, the lens returns to its uncrimped configuration, leaving a toric surface on the outer surface of the lens. This process is labor-intensive and requires great precision in the crimping.

It has been recognized in the art that the crimping process is less than desirable and efforts have been made to provide for the manufacture of toric lenses without crimping. For example, U.S. Pat. No. 4,680,998 of Council, Jr. (assigned to Bausch & Lomb, Inc.) relates to "TORIC LENSES, METHOD AND APPARATUS FOR MAKING SAME". The '998 patent describes a lathe apparatus in which a lens blank is chucked to a spindle and the spindle rotated. A cutting tool is supported on a rotary quadrant whose rotational swing moves the cutting tool arcuately across the face of the lens blank. In this way, the cutting tool is moved through a predetermined tool path in order to cut the lens as the spindle rotates. Furthermore, the precise, momentary angular position of the lens is monitored as the lens rotates on the spindle and the cutting tool is oscillated as necessary in synchronization with the angular position of the lens in order to provide a non-spherical surface on the lenses. Of course, normally, as a workpiece is turned in a conventional lathe, the resulting product has a surface of revolution matching the path taken by the tip of the cutting tool. By selectively oscillating the cutting tool during the rotation of the workpiece, some parts of the surface can be truly a surface of revolution (axisymmetric), while other parts can be non-axisymmetric. The '998 patent discloses the use of an electric motor) to effect a rotary oscillation of a vertically oriented tool post (100) about the motor shaft (99). With the cutting tool (36) being mounted on the tool post, rotary oscillation of the cutting tool is effected. One disadvantage of this arrangement is that the useful magnitude (useful stroke) of the cutting tool's oscillations is severely limited because as the magnitude of the oscillations increases, the position of the cutting tool varies relative to the lens blank. This tends to limit the lenses that can be made with this arrangement.

U.S. Pat. Nos. 4,884,482 and 4,947,715, each of *Council, Jr.* (and each assigned to City Crown, Inc. of Tampa, Fla.), relate to method and apparatus for cutting an aspheric surface on a workpiece. The apparatus and method described in the '482 and '715 patents is quite similar to that described in the '998 patent. However, in the '482 and '715 patents, instead of oscillating the cutting tool as is described in the '998 patent, the workpiece is oscillated (by oscillating the spindle) in an effort to improve the effective useful stroke of the oscillations between the cutting tool and the workpiece. However, oscillating the workpiece is somewhat problematic. In recent years, another lathe apparatus has been placed on the market by Rank Pneumo (a division of Rank Taylor Hobson of Keene, N.H.) for generating toric lenses. The Rank Pneumo lathe apparatus includes an X-Z 2-axis (translating) quadrant. The Rank Pneumo lathe apparatus utilizes a tool servo mechanism for the production of non-axisymmetric shapes, including torics, off-axis conics, and other free form surfaces. This lathe apparatus provides a rapidly positionable linear motion (Z') which is parallel to the traditional Z axis of travel for the cutting tool. The motion is accurately coordinated with the angular position of the work-holding spindle and the linear motions of the X and Z axes to produce preprogrammed non-axisymmetrical shapes. One advantage of this apparatus over what is described in the '998 patent is that the oscillation is translational and is effected by using dual piezoelectric actuators with a lever mechanism for amplifying the motion of the actuators. The piezoelectric elements have a naturally high frequency which allows toric lens geometries to be machined at spindle speeds of up to approximately 6,000 rpm. As a result, relatively high production rates can be achieved.

The apparatus made by Rank Pneumo has an actual maximum stroke of between 0.2 mm and 0.4 nun, depending upon the rate of oscillation. Near the center of the lenses to be cut, such a limited motion often is not a serious drawback. However, out nearer the edges of the lenses, the effective stroke of the known Rank Pneumo arrangement becomes smaller due to the fact that the stroke is oriented at a substantial angle relative to the thickness of the lenses at that point.

Accordingly, it can be seen that a need yet remains for a lathe apparatus and method which allows the production of non-axisymmetric surfaces on lenses and which provides a greater effective stroke over known apparatus and techniques. It is to the provision of such a lathe apparatus and method that the present invention is primarily directed.

SUMMARY OF THE INVENTION

Briefly described, in a first preferred form the present invention comprises a lathe for manufacturing a product with a non-axisymmetric shape from a workpiece. The lathe is particularly well-suited for making contact lenses with toric surfaces. The lathe comprises a spindle for rotating the workpiece about an axis of rotation and a cutting tool for cutting the workpiece. The lathe also includes a movable bed means for supporting the cutting tool in a fixed angular orientation relative to the axis of rotation and for moving the cutting tool along a predetermined path adjacent the workpiece as the spindle rotates the workpiece. Also, means are provided for oscillating the cutting tool along an oscillation axis as the movable bed means moves the cutting tool along the predetermined path. The oscillation axis is oriented at a fixed, non-zero angle with respect to the axis of rotation.

Preferably, the oscillation axis is oriented at an angle of between about 20° and 70° with respect to the axis of rotation. More preferably, the oscillation axis is oriented at an angle of between about 30° and 60° with respect to the axis of rotation. Most preferably, the oscillation axis is oriented at a 45° angle with respect to the axis of rotation.

In another form the present invention comprises a method of manufacturing a product with a non-axisymmetric shape, such as toric contact lenses. The lathe is of the type having a spindle for rotating the workpiece about a rotation axis, a cutting tool, a non-rotary movable bed for supporting the cutting tool in a fixed angular orientation relative to the rotation axis and for moving the cutting tool along a predetermined path as the spindle rotates the workpiece, and a device for oscillating the cutting tool along an oscillation axis. The improvement therein comprises that the device for oscillating the cutting tool is oriented such that the oscillation axis is oriented at an oblique, fixed angle with respect to the rotation axis. Most preferably, the oblique angle is about 45°.

In another form the present invention comprises a method of manufacturing products having a non-axisymmetric shape from a workpiece, such as for making toric lenses, and the method is carried out using a lathe with a cutting tool. The method comprises the steps of rotating the workpiece about a rotation axis, and moving the cutting tool along a predetermined path adjacent the workpiece as the workpiece is rotated while maintaining a fixed, non-zero angle between the cutting tool and the rotation axis. The method also comprises the step of, as the cutting tool is moved along the predetermined path, oscillating the cutting tool along an oscillation axis which is oriented at an oblique angle relative to the rotation axis. Most preferably, the oblique angle is approximately 45°.

In another preferred form, the invention comprises a lathe for manufacturing a product with a non-axisymmetric shape from a workpiece, such as a contact lens with one or more toric surfaces. The lathe includes a spindle for rotating the workpiece about an axis of rotation and a cutting tool. A rotary quadrant is provided for supporting the cutting tool and for moving the cutting tool arcuately along a predetermined path adjacent the workpiece as the spindle rotates the workpiece. Means are provided for oscillating the cutting tool translationally along an oscillation axis as the rotary quadrant moves the cutting tool arcuately along the predetermined path. Also, the oscillation means is mounted adjacent the rotary quadrant.

In another form, the present invention comprises a method of manufacturing products having non-axisymmetric shapes from a workpiece. The method is carried out using a lathe with a cutting tool mounted on a rotary quadrant. The method includes the steps of rotating the workpiece about a rotation axis and swinging the cutting tool arcuately along a predetermined path adjacent the workpiece as the workpiece is rotated. The method further includes the step of, as the cutting tool is swung arcuately along the predetermined path, translationally reciprocating the cutting tool relative to the workpiece.

The apparatus and method according to the present invention offers substantial advantages over known apparatus and methods. In some of the known prior art, the effective stroke of the oscillation is limited due to the fact that the oscillations occur parallel to the axis of rotation, while much of the surface of a lens to be machined is oriented such that the axis of rotation is not perpendicular to the surface at that point. In other of the known prior art, the effective stroke is limited by the rotary nature of the oscillations of the cutting tool. By contrast, the present invention obtains a greater effective use of the limited actual stroke of the known oscillation mechanisms by swinging the oscillation axis out to an angle relative to the axis of rotation and/or by oscillating the cutting tool with a translational movement.

The invention allows the manufacture of a wider range of contact lenses, including contact lenses with greater asymmetry than previously possible Accordingly, it is a primary object of the present invention to provide a lathe apparatus and method which is capable of producing a wide range of non-axisymmetric lenses.

It is another object of the present invention to provide a lathe apparatus and method which is capable of producing lenses with greater non-axisymmetry.

It is another object of the present invention to provide a lathe apparatus and method which provides a greater effective oscillation stroke using known oscillation mechanisms.

It is another object of the present invention to provide a lathe apparatus and method for producing non-axisymmetric lenses which is simple in its construction, durable in operation, and economical to manufacture and use.

These and other objects, features, and advantages of the present invention will be better understood by reading the following description in conjunction with the accompanying drawings.

BRIEF DESCRIPTION OF THE DRAWING FIGURES

FIG. 1A is a front side view of a non-axisymmetric lens which can be manufactured according to the apparatus and method of the present invention.

FIG. 1B is a left side view of the non-axisymmetric lens of FIG. 1A.

FIG. 1C is a side view of another non-axisymmetric lens which can be manufactured according to the apparatus and method of the present invention.

DETAILED DESCRIPTION OF THE PREFERRED EMBODIMENT

Figure 2:
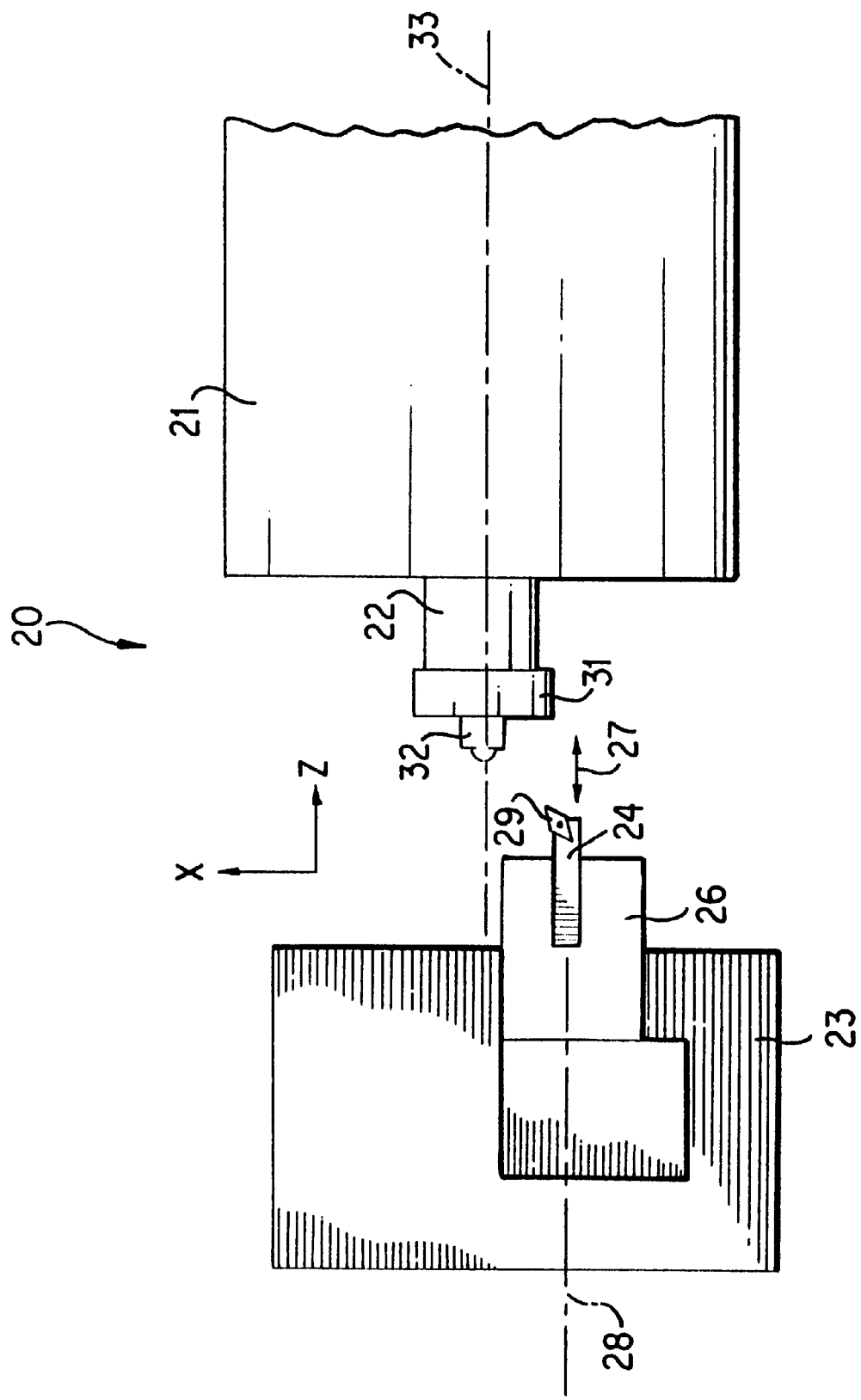
FIG. 2 is a schematic, plan view of a prior art lathe apparatus for making nonaxisymmetric lenses.

Referring now in detail to the drawing figures, wherein like reference numerals depict like parts throughout the several views, FIG. 1A through 1C depict examples of non-axisymmetric lens shapes which can be constructed using the present invention. It should be noted that these lens shapes themselves are not new and that they have been made in the past, albeit at greater cost and with greater difficulty than using the principles of the present invention.

FIG. 1A and FIG. 1B show front and left side views, respectively of a toric lens 10 having a spherical portion 11 and an aspherical portion 12. As can be seen by comparing FIGS. 1A and 1B, the aspherical portion 12 has a first radius of curvature $r_1$, in one direction and a second, quite different radius of curvature $r_2$ when viewed from a direction perpendicular thereto.

FIG. 1C shows another type of non-axisymmetry in which a toric lens 15 includes a generally spherical upper portion 16, an aspherical central portion 17 and a ballast portion 18. As can be seen in FIG. 1C, the ballast portion 18 has a thickness $t_2$ which is substantially greater than the thickness $t_1$, of the upper portion 16.

FIG. 2 shows a prior art lathe apparatus for making toric lenses of the general type made by Rank Pneumo, a division of Rank Taylor Hobson of Keene, N.H. As this lathe apparatus is commercially available and known in the art, a complete description of all of its construction details is not necessary here. Prior art lathe apparatus 20 includes an unshown base and a spindle housing 21 supported thereupon. The spindle housing 21 houses and supports a rotatable spindle 22 driven by an unshown motor means. As is already known in the art, the lathe apparatus 20 also includes sensor means for detecting the instantaneous angular position of the spindle for coordinating the movements of the cutting tool.

The prior art lathe apparatus 20 also includes a two-axis movable bed or quadrant 23. A tool holder 24 is supported by a tool holder support housing 26 which in turn is mounted to the quadrant 23. The tool holder support housing 26 houses internal (unshown) oscillation means for oscillating the tool holder back and forth in the direction of double-headed direction arrow 27 along oscillation axis 28. In this way, a cutting tool 29, which is mounted to the tool holder 24, is oscillated back and forth along the oscillation axis 28.

A chuck 31 is mounted at the end of the spindle 22 for supporting a lens blank or workpiece 32. The spindle 22 rotates the workpiece 32 about rotation axis 33. As the workpiece 32 rotates about the rotation axis 33, the quadrant 23 moves through a 30 predetermined path using conventional CNC (Computer Numerical Control) principles. In doing so, the quadrant moves in the X and Z axes.

The prior art apparatus just described and shown in FIG. 2 uses dual piezoelectric actuators with a motion amplifying lever mechanism for oscillating the tool holder 24 and the cutting tool 29. The range of motion of the oscillation is 0.4 mm (less as the rate of oscillation increases). This 0.4 mm stroke limitation acts to limit the types of non-axisymmetric toric lenses that can be manufactured using such an arrangement because in many instances a stroke greater than 0.4 mm would be required in order to provide the desired asymmetry.

Figure 3:
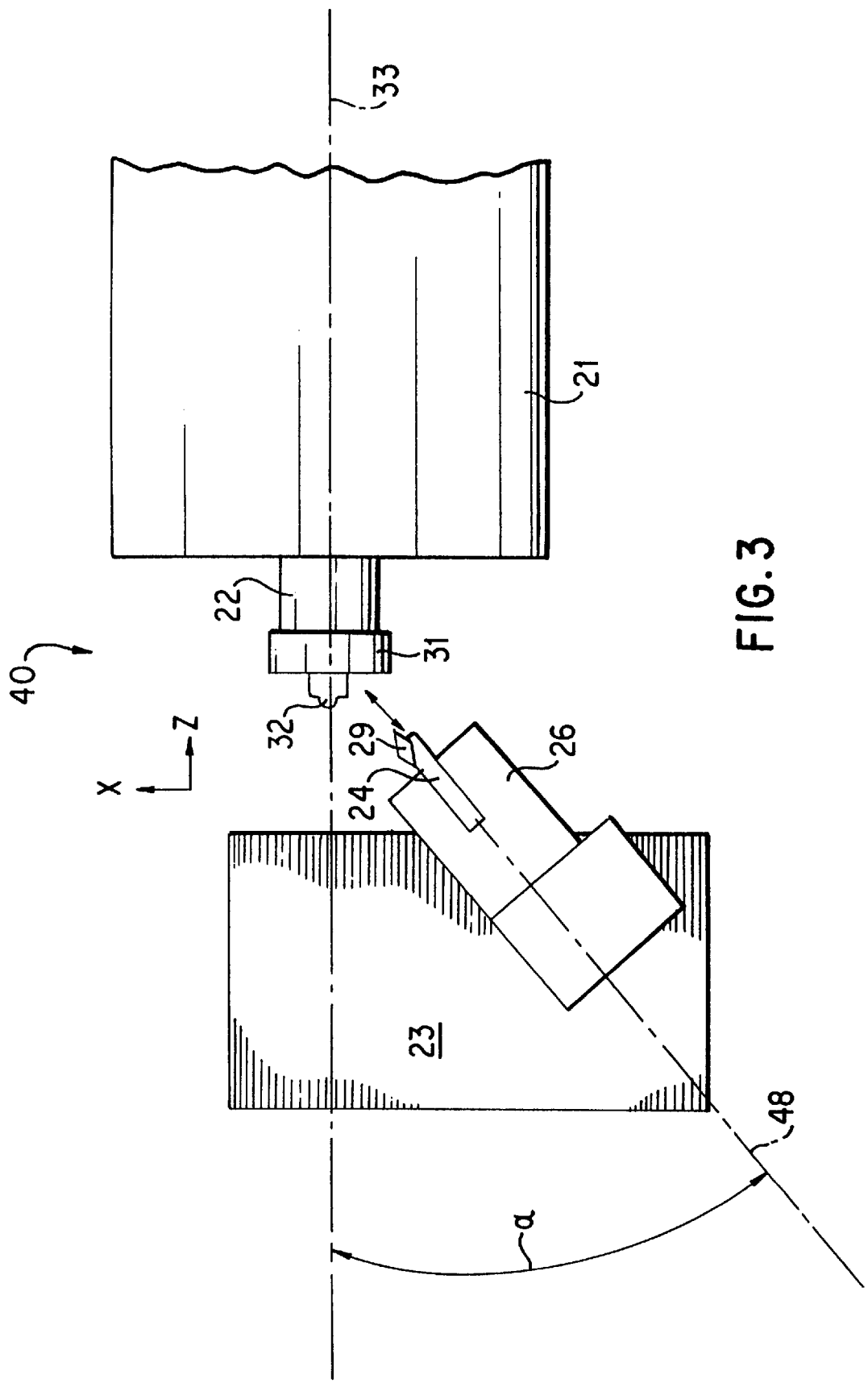
FIG. 3 is a schematic plan view of a lathe apparatus according to a preferred form of the invention for manufacturing non-axisymmetric lenses.

FIG. 3 shows the novel lathe apparatus 40 according to a preferred form of the present invention. The lathe apparatus 40 is similar in many respects to the prior art lathe apparatus 20 depicted in FIG. 2. For example, the novel lathe apparatus 40 includes an unshown base, a spindle housing 21 and a spindle 22. The lathe apparatus 40 also includes a quadrant or movable bed 23 for moving in the X and Z directions. The novel lathe apparatus 40 also includes a chuck 31 for supporting a workpiece or lens blank 32. A tool holder 24 supports a cutting tool 29 and in turn is supported by a tool holder support housing 26. Note that the angular orientation of the cutting tool 29 relative to the tool holder 24 preferably is shifted (see FIG. 3) from what is shown in FIG. 2 in order to effect an appropriate presentation of the cutting tool to the workpiece. The tool holder support housing 26 also includes the internally mounted oscillation mechanism for oscillating the tool holder (and therefore the cutting tool 29) back and forth. In this regard, the dual piezoelectric actuators preferably are used, or alternatively, a motor can be used to oscillate the tool holder as taught in U.S. Pat. No. 4,680,998. Alternatively, there may be other arrangements for oscillating the tool holder and the cutting tool.

As can be readily seen from FIG. 3, an important distinction between the novel lathe apparatus 40 and what is shown in the prior art configuration depicted in FIG. 2 is that the oscillation axis 48 according to the present invention is no longer oriented to be parallel to the rotation axis 33. Rather, the oscillation axis 48 is oriented at an oblique angle α with respect to the oscillation axis. Preferably, the oblique angle α is between about 20° and 70° with respect to the rotation axis 33. More preferably, the oblique angle α is between about 30° and 60° with respect to the rotation axis. Most preferably, the oblique angle is about 45°.

Figure 4:
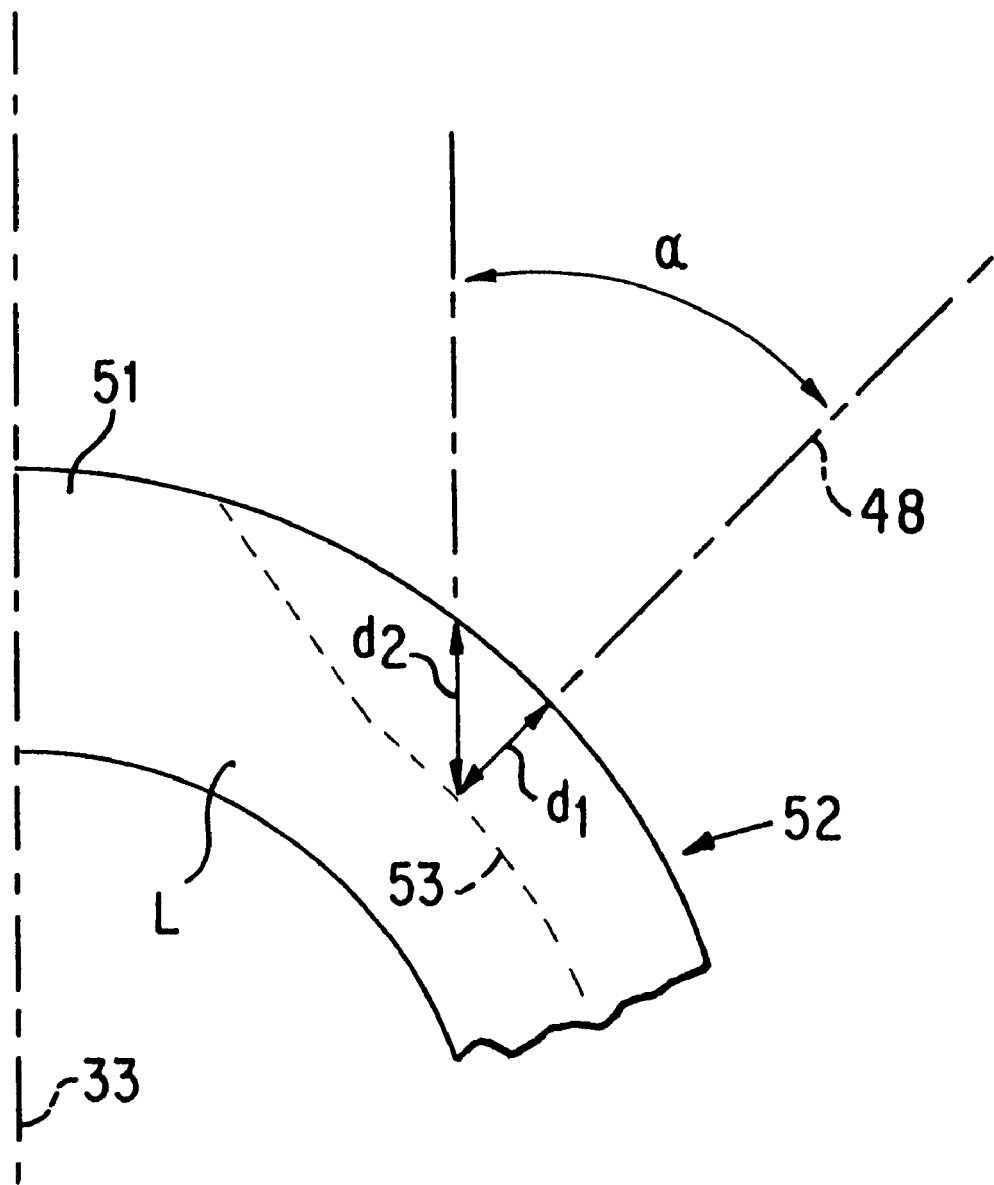
FIG. 4 is a schematic side view of a portion of a non-axisymmetric lens made according to the present invention.

FIG. 4 is useful in understanding the significance of repositioning the oscillation axis to the oblique angle α in FIG. 4, a portion of a lens L is shown in relation to the rotation axis 33. The lens L has a spherical portion 51 and an aspherical portion 52. In the aspherical portion 52, the non-axisymmetry is depicted by dash line 53. If one were to use the prior art lathe apparatus of FIG. 2 to try to produce this non-axisymmetry, the stroke of oscillation of the cutting tool would have to be greater than the distance $d_2$ in order to achieve the desired depth. However, the maximum stroke of the oscillation is less than the distance $d_2$ in many instances. By having the oscillation axis 48 be offset by the angle α from the rotation axis, to achieve the same profile, the distance $d_1$ corresponds to the necessary stroke required to achieve the profile. Simply put, the oscillation axis ideally is swung to an angle where it is perpendicular to the surface of the lens where the non-axisymmetry is required. In this way, the rather limited actual stroke of the known oscillation mechanisms is more effectively utilized to achieve a desired non-axisymmetric profile. With the tool holder being held in a fixed orientation relative to the axis of rotation, the perpendicularity is not maintained over the entirety of the surface. It is possible to construct an arrangement in which the tool holder orientation is varied during use in order to maintain true perpendicularity at all points along the surface, but at the expense of added mechanical complexity and added computational complexity.

Those skilled in the art will recognize that the software used to control the oscillations of prior art lathe apparatus must be modified to adjust for the angle α. However, the mathematical compensation required represents a straight-forward trigonometric problem. Those skilled in the art will easily recognize that while the oscillation axis is shown in FIG. 3 to be on one side of the rotation axis, it could just as easily be positioned on the other side. Furthermore, in addition to being very useful for making contact lenses (among other products), the present invention is equally useful for producing molds and other tooling for making contact lenses.

Figure 5:
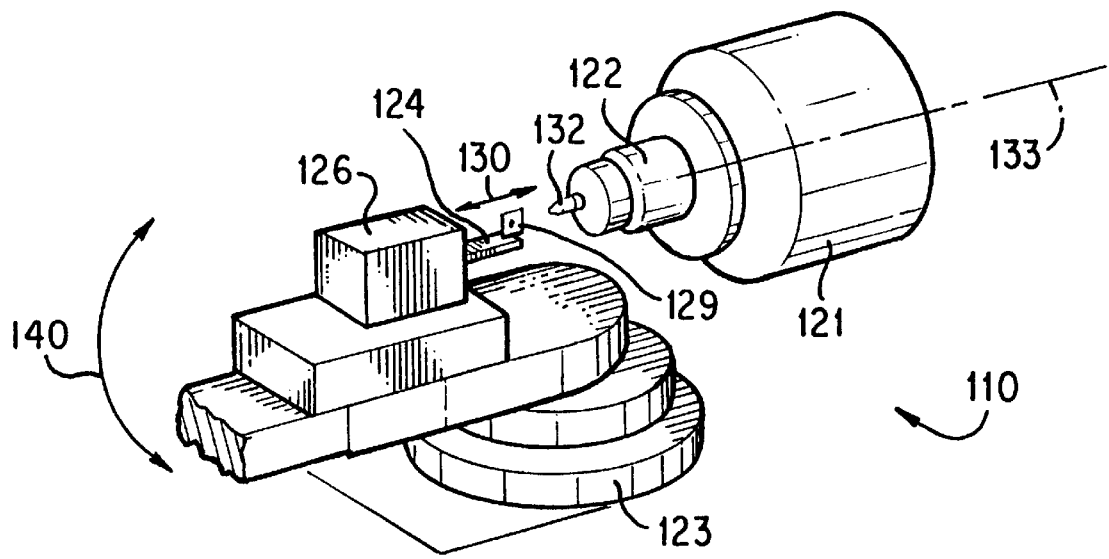
FIG. 5 is a perspective, schematic view of a lathe apparatus according to another preferred form of the invention.

FIG. 5 shows a lathe apparatus 110 according to a second preferred form of the present invention. The lathe apparatus 110 includes a spindle housing 121 and a driven spindle 122 for supporting and rotating a workpiece 132. The workpiece is rotated about an axis of rotation 133.

The lathe apparatus 110 also includes a rotary quadrant 123 supporting a housing 126. The housing 126 includes a mechanism (unshown in this figure) for reciprocating (oscillating 30 back and forth in a translational manner) a tool holder 124 which supports a cutting tool 129. In this way, the cutting tool 129 is reciprocated along movement axis 130. An upper portion of rotary quadrant 123 moves arcuately in the direction of arcuate direction arrow 140 to move the cutting tool 129 through a predetermined arcuate path adjacent the workpiece 132.

Figure 6:
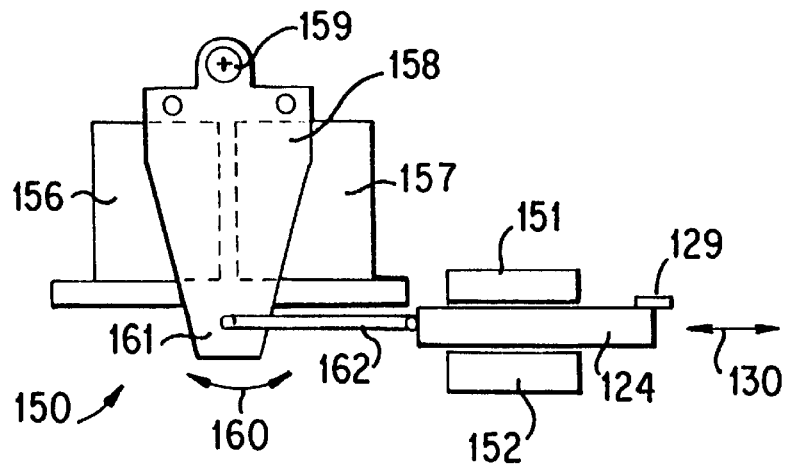
FIG. 6 is a schematic, sectional view of an oscillation mechanism portion of the lathe apparatus of FIG. 5.

FIG. 6 shows one preferred mechanism for oscillating the cutting tool 129 in a reciprocal translational manner. The oscillation mechanism 150 includes guide means 151 and 152 for guiding the tool bar 124 to restrict its motion to a reciprocating, translational motion depicted by arrow 130. Also, additional (unshown) guide means can be provided on the sides of the tool bar 124 to further restrict the movement to a translational, reciprocating motion. The mechanism 150 is of the general type employed in the Rank Pneumo device described above.

The oscillation mechanism 150 also includes a pair of piezoelectric elements 156 and 157 for causing pivotal movement of a pendulum 158 about a pivot point 159. As the height of each of the piezoelectric elements 156 and 157 rises and falls with changing voltages applied thereto, this causes the pendulum 158 to pivot about the pivot point 159 and causes the lower end 161 of the pendulum to move through an arcuate path of movement depicted by direction arrow 160. A linkage or strut 162 is pivotally connected at one end thereof to the lower end 161 of the pendulum 158 and is pivotally connected at an opposite end thereof to a backside portion of the tool bar 124. In this way, pivotal motion of the lower end 161 of the pendulum 158 is converted into translational movement of the tool bar 124. With the cutting tool 129 being fixedly secured to an upper portion of the tool bar 124, a reciprocating, translational motion of the cutting tool is achieved.

The present invention has some notable advantages over the prior art lathe apparatus having oscillation mechanisms. Firstly, for a given profile, it allows a smaller oscillation to be used to achieve the same asymmetric depth. The use of a smaller oscillation often allows the rate of oscillation to be increased, thereby allowing the spindle speed to be increased as well. This increases the productive throughput or production rate of the lathe apparatus. Moreover, the present apparatus and method also allows a greater effective use of the maximum stroke of the known oscillation mechanisms to increase the effective range of the oscillation mechanisms. Furthermore, using a reciprocating translational oscillation mechanism (See FIGS. 5 and 6) with a rotary quadrant greatly increases the utility of a rotary quadrant lathe. In other words, profiles that could not previously be made using known equipment can now be generated with the novel apparatus of the present invention.

While the invention has been disclosed in preferred forms, it will be apparent to those skilled in the art that many modifications, additions, and deletions may be made therein without departing from the spirit and scope of the invention as set forth in the following claims.

We claim:

1. A lathe for manufacturing a contact lens with a non-axisymmetric shape from a workpiece, said lens having one or more toric surfaces, said lathe comprising:

a spindle for rotating the workpiece about an axis of rotation;

a cutting tool;

movable bed means for supporting said cutting tool in a fixed angular orientation relative to said axis of rotation and for moving said cutting tool along a predetermined path adjacent the workpiece as said spindle rotates the workpiece, said movable bed means being capable of translational movement along at least a first axis and a second axis transverse to said first axis; and means for oscillating said cutting tool along an oscillation axis as said movable bed means moves said cutting tool along said predetermined path, wherein said oscillation axis is held constant at a non-zero angle $\alpha$ with respect to said axis of rotation.

2. A lathe as claimed in claim 1 wherein said oscillation axis is oriented at an angle of between about 20° and 70° with respect to said axis of rotation.

3. A lathe as claimed in claim 1 wherein said oscillation axis is oriented at an angle of between about 30° and 60° with respect to said axis of rotation.

4. A lathe as claimed in claim 1 wherein said oscillation axis is oriented at an angle of about 45° with respect to said axis of rotation.

5. A lathe as claimed in claim 1 wherein said means for oscillating said cutting tool provides translational oscillating movement of said cutting tool.

6. A method of manufacturing a lens having a non-axisymmetric shape from a workpiece, the method being carried out using a lathe with a cutting tool and comprising the steps of:

rotating the workpiece about a rotation axis;

moving the cutting tool along a predetermined path adjacent the workpiece as the workpiece is rotated, the step of moving the cutting tool along a predetermined path being carried out by translational movements of the cutting tool along at least two movement axes which are transverse to one another; and oscillating the cutting tool along an oscillation axis which is held constant at an oblique angle $\alpha$ relative to the rotation axis.

7. The method of claim 6 wherein said oblique angle is between about 20° and 70°.

8. The method of claim 6 wherein said oblique angle is between about 30° and 60°.

9. The method of claim 6 wherein said oblique angle is about 45°.

* * * * *